US008981031B2

(12) United States Patent
Miller et al.

(10) Patent No.: US 8,981,031 B2
(45) Date of Patent: Mar. 17, 2015

(54) PHOTO-PATTERNABLE DIELECTRIC MATERIALS CURABLE TO POROUS DIELECTRIC MATERIALS, FORMULATIONS, PRECURSORS AND METHODS OF USE THEREOF

(71) Applicant: International Business Machines Corporation, Armonk, NY (US)

(72) Inventors: Robert D. Miller, San Jose, CA (US); Alshakim Nelson, Fremont, CA (US); Jitendra S. Rathore, Campbell, CA (US); Ratnam Sooriyakumaran, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 13/742,526

(22) Filed: Jan. 16, 2013

(65) Prior Publication Data
US 2013/0197253 A1    Aug. 1, 2013

Related U.S. Application Data

(62) Division of application No. 12/575,515, filed on Oct. 8, 2009, now Pat. No. 8,389,663.

(51) Int. Cl.
| | |
|---|---|
| *C08G 77/12* | (2006.01) |
| *H01L 23/532* | (2006.01) |
| *C07F 7/21* | (2006.01) |
| *C08L 83/14* | (2006.01) |
| *G03F 7/075* | (2006.01) |
| *G03F 7/40* | (2006.01) |
| *H01L 21/02* | (2006.01) |
| *H01L 21/31* | (2006.01) |
| *H01L 21/768* | (2006.01) |
| *C08G 77/50* | (2006.01) |
| *G03F 7/004* | (2006.01) |

(52) U.S. Cl.
CPC .............. *H01L 23/5329* (2013.01); *C07F 7/21* (2013.01); *C08L 83/14* (2013.01); *G03F 7/0757* (2013.01); *G03F 7/40* (2013.01); *H01L 21/02126* (2013.01); *H01L 21/02137* (2013.01); *H01L 21/02203* (2013.01); *H01L 21/02282* (2013.01); *H01L 21/31* (2013.01); *H01L 21/76802* (2013.01); *H01L 21/76808* (2013.01); *H01L 21/76814* (2013.01); *G03F 7/0755* (2013.01); *C08G 77/50* (2013.01); *G03F 7/0045* (2013.01)
USPC .............................. 528/41; 556/440; 556/479

(58) Field of Classification Search
CPC ....... C08F 7/1836; C08K 5/101; C07C 67/055
USPC ..................................... 528/41; 556/440, 479
See application file for complete search history.

(56) References Cited

U.S. PATENT DOCUMENTS

| | | | |
|---|---|---|---|
| 2,823,218 A * | 2/1958 | Speier et al. .................. 556/415 |
| 3,776,977 A * | 12/1973 | Chadha ....................... 525/100 |
| 6,087,064 A | 7/2000 | Lin et al. |
| 6,143,360 A | 11/2000 | Zhong |
| 6,184,260 B1 | 2/2001 | Zhong |
| 6,770,726 B1 | 8/2004 | Arkles et al. |
| 7,041,748 B2 | 5/2006 | Lin et al. |
| 7,056,840 B2 | 6/2006 | Miller et al. |
| 7,306,853 B2 | 12/2007 | Lin et al. |
| 7,345,000 B2 | 3/2008 | Kevwitch et al. |
| 7,405,168 B2 | 7/2008 | Lee et al. |
| 7,468,330 B2 | 12/2008 | Allen et al. |
| 7,867,689 B2 | 1/2011 | Allen et al. |
| 7,919,225 B2 | 4/2011 | Allen et al. |
| 2004/0137241 A1 | 7/2004 | Lin et al. |
| 2006/0183055 A1 | 8/2006 | O'Neill et al. |
| 2007/0077782 A1 | 4/2007 | Lee et al. |
| 2008/0044664 A1 | 2/2008 | Shirato et al. |
| 2008/0063880 A1 | 3/2008 | Lin et al. |
| 2008/0076262 A1 | 3/2008 | Kevwitch et al. |
| 2008/0199789 A1 | 8/2008 | Abdallah et al. |
| 2011/0083887 A1 | 4/2011 | Brock et al. |

FOREIGN PATENT DOCUMENTS

| | | |
|---|---|---|
| JP | 2005232024 | 9/2005 |
| WO | 2005114724 | 12/2005 |

OTHER PUBLICATIONS

Satoshi Mikoshiba and Shuzi Hayase; Preparation of low density poly(methylsilsesquioxane)s for LSI interlayer dielectrics with low dielectric constant. Fabrication of Angstrom size pores prepared by baking trifluoropropylsilyl copolymers; Received Sep. 10, 1998, Accepted Nov. 23, 1998; J. Mater. Chem., 1999, v.9, pp. 591-598.

Ezbiansky et al., β-Acetoxyethyl Silsesquioxanes: Chloride-Free Precursors for SIO2 Films Via Staged Hydrolysis; Mat. Res. Soc. Symp. Proc. vol. 606 (C) 2000 Materials Research Society; pp. 251-256.

Office Action (Mail Date Jun. 19, 2012) for U.S. Appl. No. 12/575,515, filed Oct. 8, 2009.

Amendment filed Sep. 13, 2012 in response to Office Action (Mail Date Jun. 19, 2012) for U.S. Appl. No. 12/575,515, filed Oct. 8, 2009.

Notice of Allowance (Mail Date Oct. 26, 2012) for U.S. Appl. No. 12/575,515, filed Oct. 8, 2009.

Ex parte Matz (Bd. Pat. App. & Int. 2010)(Appeal No. 2009-9 5123 ); 9 pages.

Amendment filed Oct. 28, 2014 in response to Final Office Action (Mail Date Sep. 4, 2014) for U.S. Appl. No. 13/742,490, filed Jan. 16, 2013.

Final Office Action (Mail Date Sep. 4, 2014) for U.S. Appl. No. 13/742,490, filed Jan. 16, 2013.

(Continued)

*Primary Examiner* — Kuo-Liang Peng
(74) *Attorney, Agent, or Firm* — Schmeiser, Olsen & Watts (57) ABSTRACT

Silsesquioxane polymers that cure to porous silsesquioxane polymers, silsesquioxane polymers that cure to porous silsesquioxane polymers in negative tone photo-patternable dielectric formulations, methods of forming structures using negative tone photo-patternable dielectric formulations containing silsesquioxane polymers that cure to porous silsesquioxane polymers, structures containing porous silsesquioxane polymers and monomers and method of preparing monomers for silsesquioxane polymers that cure to porous silsesquioxane polymers.

13 Claims, 5 Drawing Sheets

(56) References Cited

OTHER PUBLICATIONS

Notice of Allowance (Mail Date Sep. 22, 2014) for U.S. Appl. No. 13/742,465, filed Jan. 16, 2013.
Amendment filed Aug. 8, 2014 in response to Office Action (Mail Date May 9, 2014) for U.S. Appl. No. 13/742,465, filed Jan. 16, 2013.
Amendment filed Jul. 9, 2014 in response to Office Action (Mail Date Apr. 16, 2014) for U.S. Appl. No. 13/742,490, filed Jan. 16, 2013.
Office Action (Mail Date Apr. 16, 2014) for U.S. Appl. No. 13/742,490, filed Jan. 16, 2013.
Office Action (Mail Date May 9, 2014) for U.S. Appl. No. 13/742,465, filed Jan. 16, 2013.

* cited by examiner

FIG. 4

PHOTO-PATTERNABLE DIELECTRIC MATERIALS CURABLE TO POROUS DIELECTRIC MATERIALS, FORMULATIONS, PRECURSORS AND METHODS OF USE THEREOF

RELATED APPLICATIONS

This application is a division of U.S. patent application Ser. No. 12/575,515 filed on Oct. 8, 2009, now U.S. Pat. No. 8,389,663 issued Mar. 5, 2013.

FIELD OF THE INVENTION

The present invention relates to the field of photo-patternable porous dielectric materials; more specifically, it relates to porous patternable dielectric materials that become porous upon curing, photo-sensitive formulations containing patternable dielectric materials that become porous upon curing, methods of using photo-sensitive formulations containing patternable dielectric materials that become porous upon curing in the fabrication of integrated circuits, integrated circuit structures comprising porous dielectric materials and monomers and methods of preparing monomers for patternable dielectric materials that become porous upon curing.

BACKGROUND OF THE INVENTION

Integrated circuits include, for example, active devices such as field effect transistors partially formed in a semiconductor substrate and interconnected by wiring levels comprising wires formed in interlevel dielectric layers formed on the substrate. Conventional wiring levels are formed by depositing an interlevel dielectric layer, patterning a photoresist layer formed on the dielectric layer, etching trenches in the dielectric layer, removing the photoresist and filling the trenches with metal. This is an expensive and time-consuming process. Accordingly, there exists a need in the art to mitigate the deficiencies and limitations described hereinabove.

SUMMARY OF THE INVENTION

A first aspect of the present invention is a composition of matter comprising: a silsesquioxane polymer comprising (i) three monomers of the structural formulas (1), (2) and (3) or (ii) three monomers of the structural formulas (1), (2) and (4) or (iii) four monomers of the of the structural formulas (1), (2), (3) and (4):

(1)

(2)

(3)

(4)

wherein $R^1$ is selected from the group consisting of linear alkyl, branched alkyl, cycloalkyl, aromatic, arene and ester moieties, each containing 1 to 20 carbon atoms; wherein $R^2$ is an alkyl moiety containing 1 to 20 carbon atoms; wherein $R^3$ is selected from the group consisting of linear alkyl, branched alkyl and cycloalkyl moieties, each containing 1 to 20 carbon atoms; and wherein m, n, o, and p represent the mole percent (mol %) of repeating units with m+n+o+p equal to or greater than about 40 mol % and wherein when only three monomers are present either p is zero or o is zero.

A second aspect of the present invention is a photoactive formulation, comprising: a photoacid generator; a casting solvent; and a silsesquioxane polymer comprising (i) three monomers of the structural formulas (1), (2) and (3) or (ii) three monomers of the structural formulas (1), (2) and (4) or (iii) four monomers of the of the structural formulas (1), (2), (3) and (4):

(1)

(2)

(3)

(4)

wherein $R^1$ is selected from the group consisting of linear alkyl, branched alkyl, cycloalkyl, aromatic, arene and ester moieties, each containing 1 to 20 carbon atoms; wherein $R^2$ is an alkyl moiety containing 1 to 20 carbon atoms; wherein $R^3$ is selected from the group consisting of linear alkyl, branched alkyl and cycloalkyl moieties, each containing 1 to 20 carbon atoms; and wherein m, n, o, and p represent the mole percent (mol %) of repeating units with m+n+o+p equal to or greater than about 40 mol % and wherein when only three monomers are present either p is zero or o is zero.

A third aspect of the present invention is a method, comprising: (a) forming on a substrate, a layer of a photoactive formulation comprising: a photoacid generator; a casting solvent; and a silsesquioxane polymer; (b) patternwise exposing the layer with light to generate an exposed layer; (c) baking the exposed layer to cross-link the silsesquioxane polymer in regions of the exposed layer exposed to the light to generate a baked layer; (d) developing the baked layer to remove portions of the baked layer not exposed to the light to form a first trench in a developed layer; (e) curing the developed layer to generate porosity in the silsesquioxane polymer and form a porous patterned cured layer including the first trench; and (f) filling the first trench in the porous patterned cured layer with an electrically conductive material.

A fourth aspect of the present invention is a structure, comprising: a cross-linked layer of a porous silsesquioxane polymer on a substrate; a trench in said cross-linked layer; an electrically conductive material filling said trench and contacting said substrate in a bottom of said trench; and said porous silsesquioxane polymer comprising (i) three monomers of the structural formulas (1), (7) and (4) or (ii) three monomers of the structural formulas (1), (7) and (3) or (iii) four monomers of the structural formulas (1), (7), (3) and (4):

wherein $R^1$ is selected from the group consisting of linear alkyl, branched alkyl, cycloalkyl, aromatic, arene and ester moieties, each containing 1 to 20 carbon atoms; wherein $R^3$ is selected from the group consisting of linear alkyl, branched alkyl and cycloalkyl moieties, each containing 1 to 20 carbon atoms; and wherein m, q, o, and p represent the mole percent (mol %) of repeating units with m+q+o+p equal to or greater than about 40 mol % and wherein when only three monomers are present p is zero or o is zero.

A fifth aspect of the present invention is a composition of matter consisting of:

wherein $R^5$ is an alkyl moiety containing 1 to 20 carbon atoms and $R^6$ is selected from the group consisting of halogens, alkanoates, amines, and alkoxides with the proviso that when $R^5$ is methyl, $R^6$ is not —Cl or —O—$C_2H_5$.

A sixth aspect of the present invention is a method of preparing an ethylalkanoate silyl compound, wherein said compound comprises:

wherein $R^5$ is an alkyl moiety containing 1 to 20 carbon atoms and $R^6$ is selected from the group consisting of halogens, alkanoates, amines, and alkoxides; and
the method comprising:
adding a compound of the structure:

to a compound of the structure:

in the presence of a chloroplatinic acid.

These and other aspects of the invention are described below.

BRIEF DESCRIPTION OF THE DRAWINGS

The features of the invention are set forth in the appended claims. The invention itself, however, will be best understood by reference to the following detailed description of an illustrative embodiment when read in conjunction with the accompanying drawings, wherein:

DETAILED DESCRIPTION

The present invention describes silsesquioxane polymers that may be mixed with one or more photoacid generators, an optional casting solvent and one or more optional additives to form a negative tone photo-patternable dielectric formulation that becomes porous upon curing. The silsesquioxane polymers of embodiments of the present invention may be linear polymers, branched polymers, caged polymers or combinations of thereof. The silsesquioxane polymers of embodiments of the present invention are preferably aqueous base soluble. Patternwise exposure of a layer of the formulation directly forms a cross-linked patterned dielectric layer (without the use of photoresist based lithography or etching of the dielectric layer) after development. After curing the patterned dielectric layer, a porous low dielectric constant (k) patterned dielectric layer is produced. A low-k material is defined as a material having a dielectric constant of about 3.0 or less.

The silsesquioxane polymers of the present invention preferably contain silanol endgroups with silyl ethers and silyl alcohols preferred (and may contain monomers having silanol moieties with silyl ethers and silyl alcohols preferred) which undergo cross-linking via condensation in the presence of acid released by the photoacid generator after exposure to light (heat increases the efficiency of the reaction). The silsesquioxane polymers according to embodiments of the present invention may also include halosilane, acetoxysilane, silylamine, and alkoxysilane endgroups depending upon the functional endgroups of the monomers used in the polymerization reaction. Cross-linking enables the formation of chemical bonds, which can withstand standard thermal curing and subsequent curing conditions such as ultraviolet (UV)-thermal treatment.

Moreover, the silsesquioxane polymers according to embodiments of the present invention contain an ethylalkanoate side-chain functionality, which undergoes a partial decomposition reaction during curing to generate a porous low-k insulating material (k less than about 3). Further, the inventors have found that incorporating an ethyl alkanoate silsesquioxane monomers into polymers allows for higher amounts of bis-triethoxysilylethane (BTSE) monomer to be incorporated into silsesquioxane polymers containing BTSE monomers. This unexpected result allows the formation of polymers with improved mechanical properties.

The silsesquioxane polymers of the present invention are particularly useful in forming damascene and dual-damascene wires without the use of a photoresist since they can be patterned directly.

A damascene process is one in which a dielectric layer having wire trenches or via openings extending through a dielectric layer is formed, an electrical conductor of sufficient thickness to fill the trenches is deposited in the trenches and on a top surface of the dielectric, and a chemical-mechanical-polish (CMP) process is performed to remove excess conductor and make the surface of the conductor co-planar with the surface of the dielectric layer to form damascene wires (or damascene vias). When only a trench and a wire (or a via opening and a via) are formed the process is called single-damascene.

A via-first dual-damascene process (according to embodiments of the present invention) is one in which a first dielectric layer having via openings extending through the first dielectric layer are formed followed by formation of a second dielectric layer having trenches extending through the second dielectric layer and intersecting the trenches in the first dielectric layer. All via openings are intersected by integral wire trenches above, but not all trenches need intersect a via opening. An electrical conductor of sufficient thickness to fill the trenches and via openings is deposited on a top surface of the dielectric. A CMP process is performed to make the surface of the conductor in the trench co-planar with the surface of the dielectric layer to form dual-damascene wires and dual-damascene wires having integral dual-damascene vias.

In one example, silsesquioxane polymers of the embodiments of the present invention comprise (i) three monomers of the structural formulas (1), (2) and (3) or (ii) three monomers of the structural formulas (1), (2) and (4) or (iii) four monomers of the structural formulas (1), (2), (3) and (4):

wherein $R^1$ is selected from the group consisting of linear alkyl, branched alkyl, cycloalkyl, aromatic, arene and ester moieties, each containing 1 to 20 carbon atoms; $R^2$ is an alkyl moiety containing 1 to 20 carbon atoms; and $R^3$ is selected from the group consisting of linear alkyl, branched alkyl and cycloalkyl moieties, each containing 1 to 20 carbon atoms; and m, n, o, and p represent the mole percent (mol %) of repeating units. When only three monomers are present either p is zero or o is zero.

Mol % is mole-fraction times 100. 10 mol % is thus 0.1 mol fraction of the polymer.

Preferred $R^1$ moieties are selected from the group consisting of methyl, ethyl, propyl, isopropyl, cyclohexyl, and norbornyl groups. Preferred $R^2$ moieties are selected from the group consisting of methyl, ethyl, propyl, n-alkyl ($CH_3$—$(CH_2)_x$— where x is 0 to 20), isopropyl, tert-butyl, 2,2 dimethylheptyl, cyclohexyl and norbornyl groups. A preferred $R^3$ moiety is an ethyl group.

In silsesquioxane polymers according to embodiments of the present invention, $R^1$ is a carbon containing group for controlling polymer dissolution in aqueous base; $R^2$ is the alkyl group of the ethyl alkanoate for generating porosity during curing; $R^3$ is a $C_1$-$C_{20}$ hydrocarbon moiety and structural formula (3) is a bridge.

In one example, silsesquioxane polymers according to embodiments of the present invention comprise monomers of structural formulas (1), (2), (3) and (4) with m+n+o+p equal or greater than about 40 mol %, with equal to or greater than about 75% preferred, with equal to or greater than about 95% more preferred, and with equal to or greater than about 99% still more preferred.

In one example, silsesquioxane polymers according to embodiments of the present invention, m is between about 10 mol % and about 90 mol %, n is between 1 mol % and about 90 mol %, o is between about 0 mol % and about 10 mol % and p is between about 0 mol % and about 60 mol % of the final polymer composition, where 0 mol % indicates the monomer is not present in the polymer. In one example, silsesquioxane polymers according to embodiments of the present invention, m is between about 50 mol % and about 80 mol %, n is between 5 mol % and about 40 mol %, o is between about 0 mol % and about 40 mol % and p is between about 1 mol % and about 60 mol % of the final polymer composition, where 0 mol % indicates the monomer is not present in the polymer. Both o and p are not simultaneously 0 mol % for a given polymer composition.

In one example, silsesquioxane polymers of embodiments of the present invention consist essentially of (i) three monomers of the structural formulas (1), (2) and (3) or (ii) three monomers of the structural formulas (1), (2) and (4) or (iii) four monomers of the structural formulas (1), (2), (3) and (4):

wherein $R^1$ is selected from the group consisting of linear alkyl, branched alkyl, cycloalkyl, aromatic, arene and ester moieties, each containing 1 to 20 carbon atoms; $R^2$ is an alkyl moiety containing 1 to 20 carbon atoms; and $R^3$ is selected from the group consisting of linear alkyl, branched alkyl and cycloalkyl moieties, each containing 1 to 20 carbon atoms; and m+n+o+p is equal to about 100 mol %. When only three monomers are present either p is zero or o is zero.

A preferred first silsesquioxane polymer consists essentially of monomers of structural formulas (1), (2), (3) and (4), $R^1$ is a methyl moiety and m is between about 40 mol % and about 70 mol %, $R^2$ is a methyl moiety and n is between about 5 mol % and about 15 mol %, $R^3$ is an ethyl moiety and o is between about 10 mol % and about 30 mol %, and p is between about 5 mol % and about 15 mol %.

A preferred second silsesquioxane polymer consists essentially of monomers of structural formulas (1), (2), (3) and (4), $R^1$ is a methyl moiety and m is between about 40 mol % and about 70 mol %, $R^2$ is an tert-butyl moiety and n is between about 5 mol % and about 15 mol %, $R^3$ is an ethyl moiety and o is between about 10 mol % and about 30 mol %, and p is between about 5 mol % and about 15 mol %.

A preferred third silsesquioxane polymer, consists essentially of monomers of structural formulas (1), (2), (3) and (4), $R^1$ is a methyl moiety and m is between about 40 mol % and about 70 mol %, $R^2$ is an neodecanyl moiety and n is between about 5 mol % and about 15 mol %, $R^3$ is an ethyl moiety and o is between about 10 mol % and 30 mol %, and p is between about 5 mol % and about 15 mol %.

In one example, the silsesquioxane polymers of the embodiments of the present invention have a weight-averaged molecular weight between about 400 Daltons and about 500,000 Daltons. In one example, the silsesquioxane polymers of the embodiments of the present invention have a weight-averaged molecular weight between about 1,500 Daltons and about 20,000 Daltons.

Negative tone photo-patternable dielectric formulations according to embodiments of the present invention include the silsesquioxane polymers of combinations of monomers (1), (2), (3) and (4) discussed supra, aphotoacid generator (PAG), and a casting solvent. Negative tone photo-patternable dielectric formulations according to embodiments of the present invention may optionally include one or more additives such as organic bases, cross-linking agents and additive polymers.

Examples of PAGs include, but are not limited to, triphenylsulfonium nonaflate, co (trifluoro-methylsulfonyloxy)-bicyclo[2.2.1]hept-5-ene-2,3-dicarboximide (MDT), N-hydroxy-naphthalimide (DDSN), onium salts, aromatic diazonium salts, sulfonium salts, diaryliodonium salts, and sulfonic acid esters of N-hydroxyamides, imides, or combinations thereof.

Examples of casting solvents include, but are not limited to, ethoxyethylpropionate (EEP), a combination of EEP and γ-butyrolactone, propylene-glycol monomethylether acetate (PGMEA) propylene-glycol monomethylether alcohol, propyleneglycol monopropyl alcohol, propyleneglycol monopropyl acetate, ethyl lactate, or combinations thereof.

The organic base may be any suitable organic base known in the photoresist art. Examples of organic bases include, but are not limited to, tetraalkylammonium hydroxides, cetyltrimethylammonium hydroxide, 1,8-diaminonaphthalene and combinations thereof. The negative tone photo-patternable dielectric formulations of the embodiments of the present invention are not limited to any specific selection of organic base.

Examples of cross-linking agents include, but are not limited to, methylphenyltetramethoxymethyl glycouril (methylphenyl POWDERLINK), tetramethoxymethyl glycouril, methylpropyltetramethoxymethyl glycouril, and 2,6-bis(hydroxymethyl)-p-cresol.

An example of a polymer additive is the silsesquioxanes polymer having the structural formula:

wherein $R^4$ is selected from the group consisting of alkyl, cycloalkyl and aryl moieties and s is an integer between about 10 and about 1000. Many polymers of structural formula (5) are commercially available, for example, from Dow Corning, Shin-Etsu, or JSR Corporation.

In one example, the silsesquioxane polymer additive possesses silanol end groups, but may also include halosilane, acetoxysilane, silylamine, and alkoxysilane endgroups. In a preferred embodiment of the present invention the additive polymer is a silsesquioxane polymer LKD-2015 (JSR Corporation) that contains silanol end groups.

The additive polymer comprises between about 1% by weight to about 99% by weight of all polymers of the negative tone photo-patternable dielectric formulations, with between about 20% by weight and 80% by weight preferred, and between about 30% by weight and 60% by weight more preferred.

The monomer of structure (2) may be synthesized by a hydrosilation reaction between a hydridosilane and a vinyl ester:

(6)

In one example, $R^5$ is an alkyl moiety containing 1 to 20 carbon atoms and $R^6$ is selected from the group of halogens, alkanoates, amines, and alkoxides. In one example, $R^5$ is an alkyl moiety containing 1 to 20 carbon atoms and $R^6$ is selected from the group of halogens, alkanoates, amines, and alkoxides with the proviso that when $R^5$ is methyl, $R^6$ is not —Cl or —O—$C_2H_5$. In one example $R^5$ is methyl, tert-butyl or neodecanyl. In one example, the Pt catalyst is chloroplatinic acid.

Figure 1A:
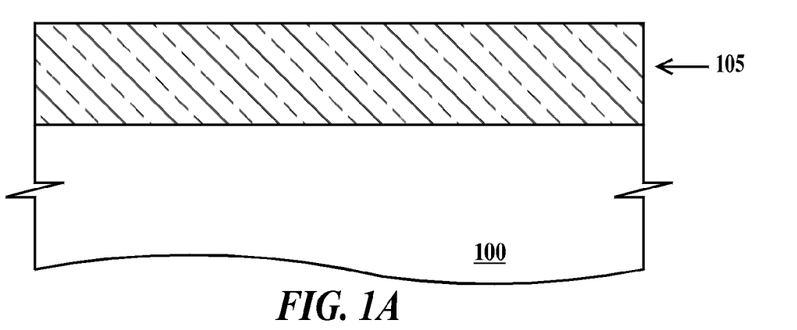
FIGS. 1A through 1C illustrate steps in a method of forming single or dual-damascene wires using a photo-patternable dielectric material according to embodiments of the present invention.
Figure 1B:
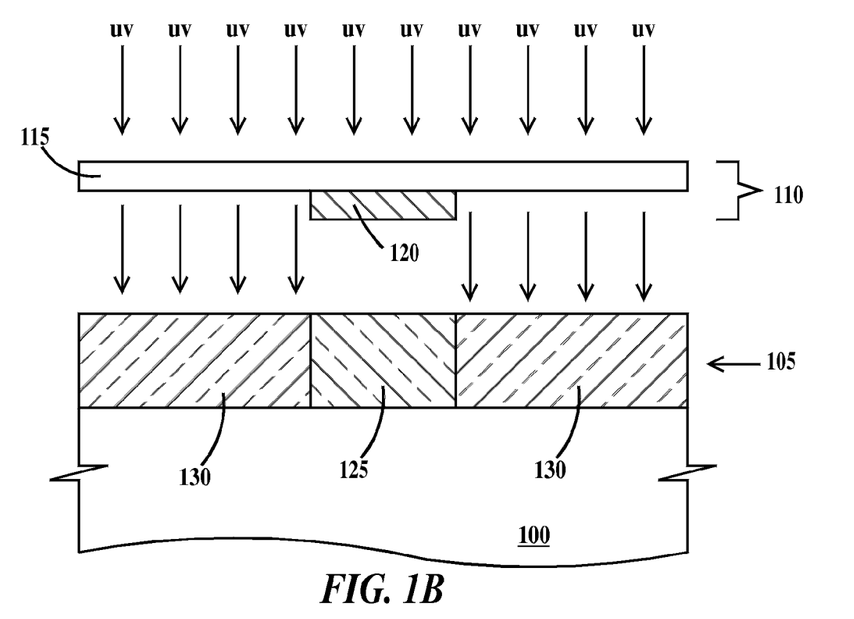
Figure 1C:
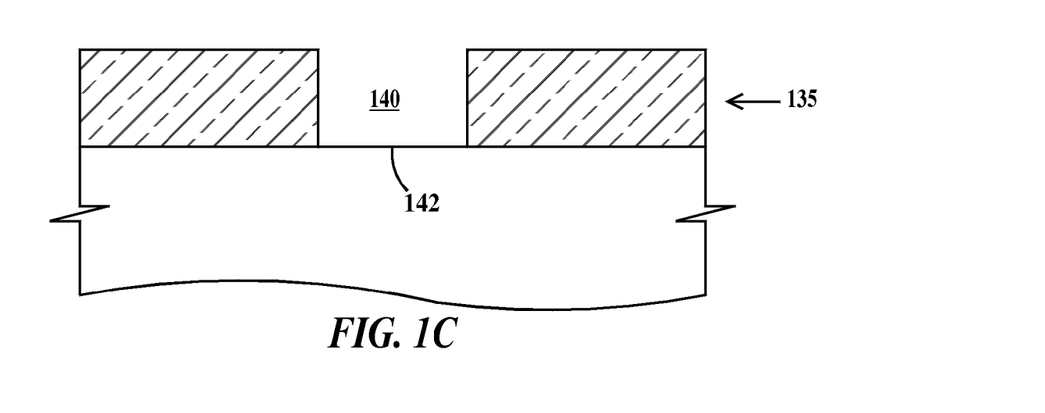

FIGS. 1A through 1C illustrate steps in a method of forming single or dual-damascene wires using a photo-patternable dielectric material according to embodiments of the present invention. In FIG. 1A, a photo-patternable dielectric layer 105 is formed on a substrate 100. Photo-patternable dielectric layer 105 is formed by spin coating, spraying or dip coating substrate 100 with a negative tone photo-patternable dielectric formulation according to embodiments of the present invention described supra. If a negative tone photo-patternable dielectric formulation includes an optional casting solvent, after applying the negative tone photo-patternable dielectric formulation a pre-exposure bake (at a temperature between about 80° C. and about 120° C. with about 110° C. preferred) is performed to drive out the casting solvent and form photo-patternable dielectric layer 105. In one example, substrate 100 includes devices such as field effect transistors, bipolar transistors, diodes, resistors, capacitors and inductors as well as contacts and damascene and/or dual-damascene wires (which wires may be formed using embodiments of the present invention or conventional processes).

In FIG. 1B, photo-patternable dielectric layer 105 is patternwise exposed to light through a mask 110. Mask 110 comprises a transparent or semi-transparent (to the wavelength of the light being used) substrate 115 having an opaque or semi-opaque to the wavelength of the light being used) image 120. More light passes through substrate 115 than through the combination of substrate 115 and image 120. One image 120 is illustrated, but there are typically hundreds of thousands to millions of such images present on a mask used to form integrated circuits. Upon exposure to the light, a pattern of unexposed regions 125 and exposed regions 130 is formed in photo-patternable dielectric layer 105. Light includes ultraviolet (UV) light (between about 10 nm and about 400 nm) and extreme UV light (between about 10 nm and about 13.5 nm). Electron beam irradiation may be used instead of UV or extreme UV light. In one example, the light has a wavelength of about 248 nm. In one example, the light has a wavelength of about 193 nm. In one example, the light has a wavelength of about 157 nm.

In FIG. 1C, a post exposure bake followed by a develop process followed by a curing process is performed to form a porous (and low k) patterned dielectric layer 135 having an opening 140 therein. A top surface 142 of substrate 140 is exposed in the bottom of opening 140. In one example, the post-exposure bake is performed at a temperature between about 35° C. and about 200° C. with a temperature between about 80° C. and about 120° C. preferred. The patternwise light (or electron beam) exposure causes the photoacid generator(s) in photo-patternable dielectric layer 105 (see FIG. 1B) to generate acid which cross-links the polymer through the hydroxyl, alkoxy, silyloxy or silanol endgroups in regions 130 (see FIG. 1B) making the polymer insoluble in basic developer. The post exposure bake enhances this cross-linking process. Suitable developers include organic or aqueous bases with aqueous basic developers preferred. In one example the developer is an aqueous solution of tetramethylammonium hydroxide. In one example, the curing process is a bake at a temperature of about 100° C. or higher. In one example, the curing process is a bake at a temperature of about 250° C. or higher. In one example, the curing process is a UV exposure using light of a wavelength between about 50 nm and about 300 nm. In one example, the curing process includes simultaneous exposure to UV light at a wavelength between about 50 nm and about 300 nm and heating to about 100° C. or higher. In one example, the curing process includes simultaneous exposure to UV light at a wavelength between about 50 nm and about 300 nm and heating to about 250° C. or higher.

The curing process causes the loss of the ethylalkanoate group of structure (2) via decomposition of the ethylalkanoate to release ethylene and an organic acid, while simultaneously generating structure 7.

(2)        (7)

The inventors unexpectedly found that curing a dielectric layer containing a silsesquioxane polymer having structure (2) or (6) forms a porous dielectric film. The dielectric constant (k) is less than 3.0. In one example, the dielectric constant of the film is less than 2.5.

Thus, after curing the now porous silsesquioxane polymer comprises (i) three monomers of the structural formulas (1), (7) and (4) or (ii) three monomers of the structural formulas (1), (7) and (3) or (iii) four monomers of the structural formulas (1), (7), (3) and (4):

(1)

-continued (7)

(3)

(4)

wherein $R^1$ is selected from the group consisting of linear alkyl, branched alkyl, cycloalkyl, aromatic, arene and ester moieties, each containing 1 to 20 carbon atoms; wherein $R^3$ is selected from the group consisting of linear alkyl, branched alkyl and cycloalkyl moieties, each containing 1 to 20 carbon atoms; and wherein m, q, o, and p represent the mole percent (mol %) of repeating units with m+q+o+p equal to or greater than about 40 mol %, with equal to or greater than about 75% preferred, with equal to or greater than about 95% more preferred, and with equal to or greater than about 99% still more preferred and wherein when only three monomers are present either p is zero or o is zero.

In one example, porous silsesquioxane polymers according to embodiments of the present invention, m is between about 10 mol % and about 90 mol %, q is between 1 mol % and about 90 mol %, o is between about 0 mol % and about 10 mol % and p is between about 0 mol % and about 60 mol % of the cured polymer, where 0 mol % indicates the monomer is not present in the polymer. In one example, porous silsesquioxane polymers according to embodiments of the present invention, m is between about 50 mol % and about 80 mol %, q is between 5 mol % and about 40 mol %, o is between about 0 mol % and about 40 mol % and p is between about 1 mol % and about 60 mol % of the cured polymer, where 0 mol % indicates the monomer is not present in the polymer.

In one example, the porous silsesquioxane polymers of embodiments of the present invention consist essentially of (i) three monomers of the structural formulas (1), (7) and (3) or (ii) three monomers of the structural formulas (1), (7) and (4) or (iii) four monomers of the structural formulas (1), (7), (3) and (4):

(1)

(7)

(3)

(4)

wherein $R^1$ is selected from the group consisting of linear alkyl, branched alkyl, cycloalkyl, aromatic, arene and ester moieties, each containing 1 to 20 carbon atoms; $R^3$ is selected from the group consisting of linear alkyl, branched alkyl and cycloalkyl moieties, each containing 1 to 20 carbon atoms; and m+q+o+p is equal to about 100 mol %. When structure (4) is not present p is 0. When structure (3) is not present, o is zero.

A preferred porous silsesquioxane polymer, consists essentially of monomers of structural formulas (1), (7), (3) and (4), $R^1$ is a methyl moiety and m is between about 40 mol % and about 70 mol %, q is between about 5 mol % and about 15 mol %, and $R^3$ is an ethyl moiety and o is between about 10 mol % and about 30 mol %, and p is between about 5 mol % and about 15 mol %.

Figure 2A:
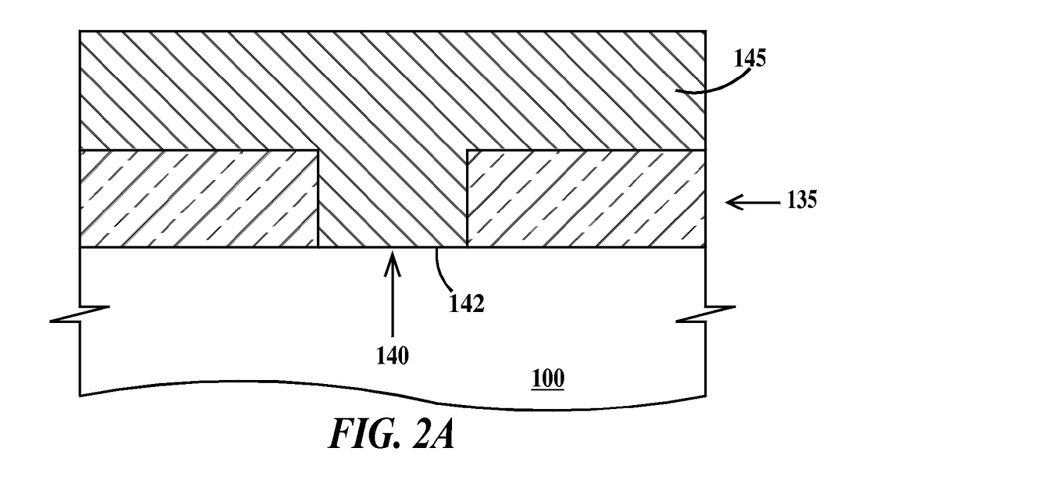
FIGS. 2A and 2B illustrate steps in a method of forming single damascene wires in a photo-patternable dielectric material according to embodiments of the present invention.
Figure 2B:
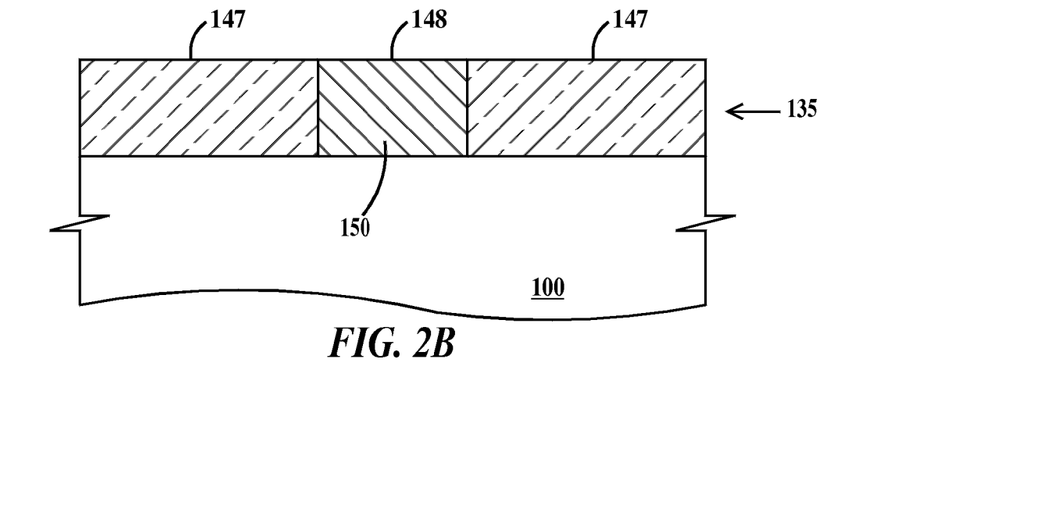

FIGS. 2A and 2B illustrate steps in a method of forming single damascene wires in a photo-patternable dielectric material according to embodiments of the present invention. FIG. 2A continues from FIG. 1C.

In FIG. 2A, a layer 145 of electrically conductive material is formed on the top surface of patterned dielectric layer 135 and the top surface 142 of substrate 100 exposed in opening 140. Layer 145 completely fills opening 140. In one example, layer 145 comprises one or more layers of metal. In one example, layer 145 comprises a conformal layer of tantalum nitride in contact with patterned dielectric layer 135 (including the sidewalls of opening 140) and substrate 100, a conformal layer of tantalum on the tantalum nitride layer, and a copper layer (i.e., core) on the tantalum layer.

In FIG. 2B, planarization process (e.g., a chemical-mechanical-polish (CMP)) is performed so a top surface 147 of patterned dielectric layer 135 is coplanar with a top surface 148 of single-damascene wire (or contact) 150. Wire 150 may electrically contact a device (e.g., a gate electrode of an FET) or another wire of a lower wiring level in substrate 100.

Figure 3A:
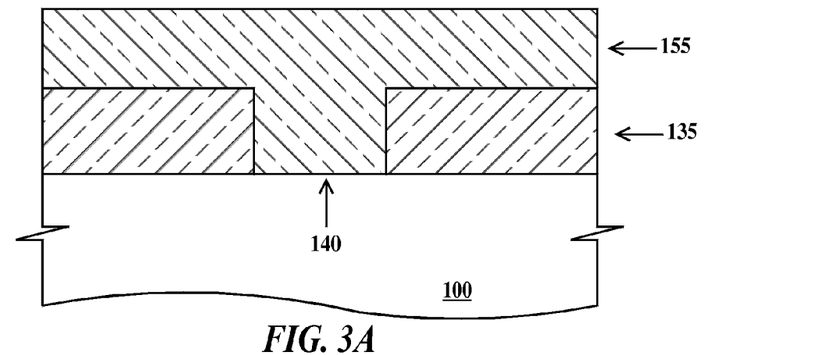
FIGS. 3A through 3E illustrate steps in a method of forming dual-damascene wires in a photo-patternable dielectric material according to embodiments of the present invention.
Figure 3B:
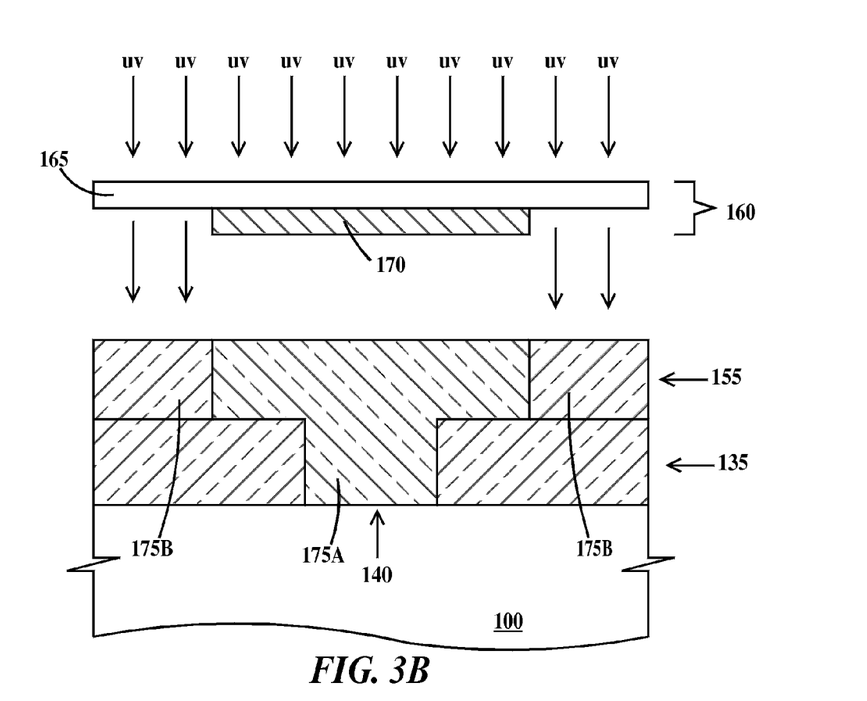
Figure 3C:
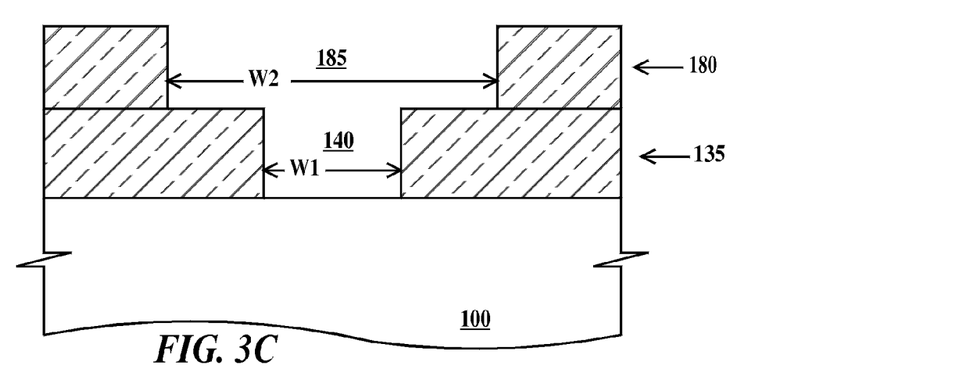

FIGS. 3A through 3C illustrate steps in a method of forming dual-damascene wires in a photo-patternable dielectric material according to embodiments of the present invention. FIG. 3A continues from FIG. 1C.

In FIG. 3A, a photo-patternable dielectric layer 155 is formed on a patterned dielectric layer 135 filling opening 140. Photo-patternable dielectric layer 155 is formed by spin coating, spraying or dip coating substrate 100 with a negative tone photo-patternable dielectric formulation according to embodiments of the present invention described supra. If a negative tone photo-patternable dielectric formulation includes a optional casting solvent, after applying the negative tone photo-patternable dielectric formulation a pre-exposure bake (e.g., at a temperature between about 80° C. and about 120° C. with about 110° C. preferred) is performed to drive out the casting solvent and form photo-patternable dielectric layer 155.

In FIG. 3B, photo-patternable dielectric layer 155 is patternwise exposed to light through a mask 160. Mask 160 comprises a transparent or semi-transparent (to the wavelength of the light being used) substrate 165 having an opaque or semi-opaque (to the wavelength of the light being used) image 160. More light passes through substrate 165 than through the combination of substrate 165 and image 170. One image 160 is illustrated, but there are typically hundreds of thousands to millions of such images present on a mask used to form integrated circuits. Upon exposure to the light, a pattern of unexposed regions 175A and exposed regions 175B is formed in photo-patternable dielectric layer 155.

In FIG. 3C, a post exposure bake followed by a develop process followed by a curing process is performed to form a porous patterned dielectric layer 180 having an opening 185 therein. Opening 140 in patterned dielectric layer 135 is exposed in the bottom of opening 185. Opening 140 has a width W1 and opening 185 has a width W2 with W2>W1. In one example, the post-exposure bake is performed at a temperature between about 35° C. and about 200° C., with a temperature between about 80° C. and about 120° C. preferred. The patternwise exposure to light causes the photoacid generator(s) in photo-patternable dielectric layer 155 (see FIG. 3B) to generate acid which cross-links the polymer through the hydroxyl, alkoxy, silyloxy or silanol endgroups in regions 175B (see FIG. 3B) making the polymer insoluble in basic developer. The post exposure bake enhances this cross-linking process. In one example, the curing process is a bake at a temperature of about 100° C. or higher. In one example, the curing process is a bake at a temperature of about 250° C. or higher. In one example, the curing process is a UV exposure using light of a wavelength between about 50 nm and about 300 nm. In one example, the curing process includes simultaneous exposure to UV light at a wavelength between about 50 nm and about 300 nm and heating to about 100° C. or higher. In one example, the curing process includes simultaneous exposure to UV light at a wavelength between about 50 nm and about 300 nm and heating to about 250° C. or higher. Again, the loss of the ethylalkonate group generates the porosity in a porous patterned dielectric layer 180.

Figure 3D:
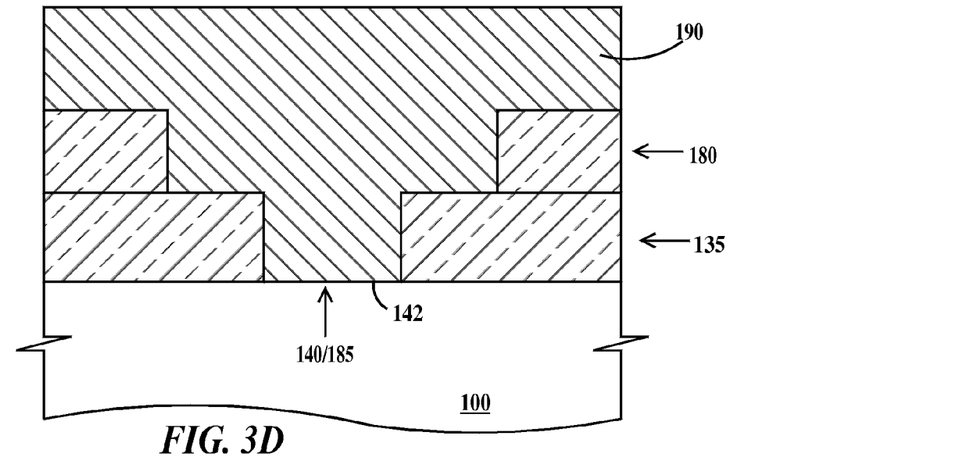

In FIG. 3D, a layer 190 of electrically conductive material is formed on the top surface of patterned dielectric layer 180, exposed surfaces of patterned dielectric layer 135, and the top surface 142 of substrate 100 exposed in opening 140. Layer 190 completely fills openings 140 and 185. In one example, layer 190 comprises one or more layers of metal. In one example, layer 190 comprises a conformal layer of tantalum nitride in contact with patterned dielectric layers 135 and 180 (including the sidewalls of openings 140 and 180 and the top surface of patterned dielectric that was exposed in opening 185 in FIG. 3C) and substrate 100, a conformal layer of tantalum on the tantalum nitride layer, and a copper layer (i.e., core) on the tantalum layer.

Figure 3E:
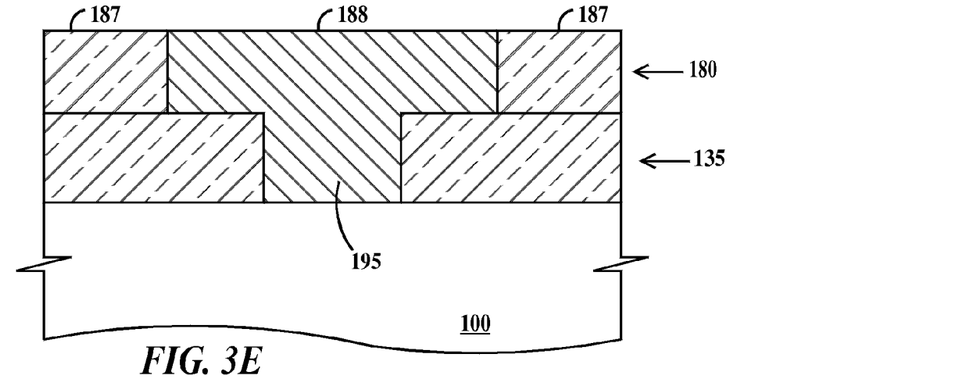

In FIG. 3E, a planarization process (e.g., a CMP) is performed so a top surface 187 of patterned dielectric layer 180 is coplanar with a top surface 188 of a dual-damascene wire 195. Wire 195 may electrically contact another wire of a lower wiring level in substrate 100.

Figure 4:
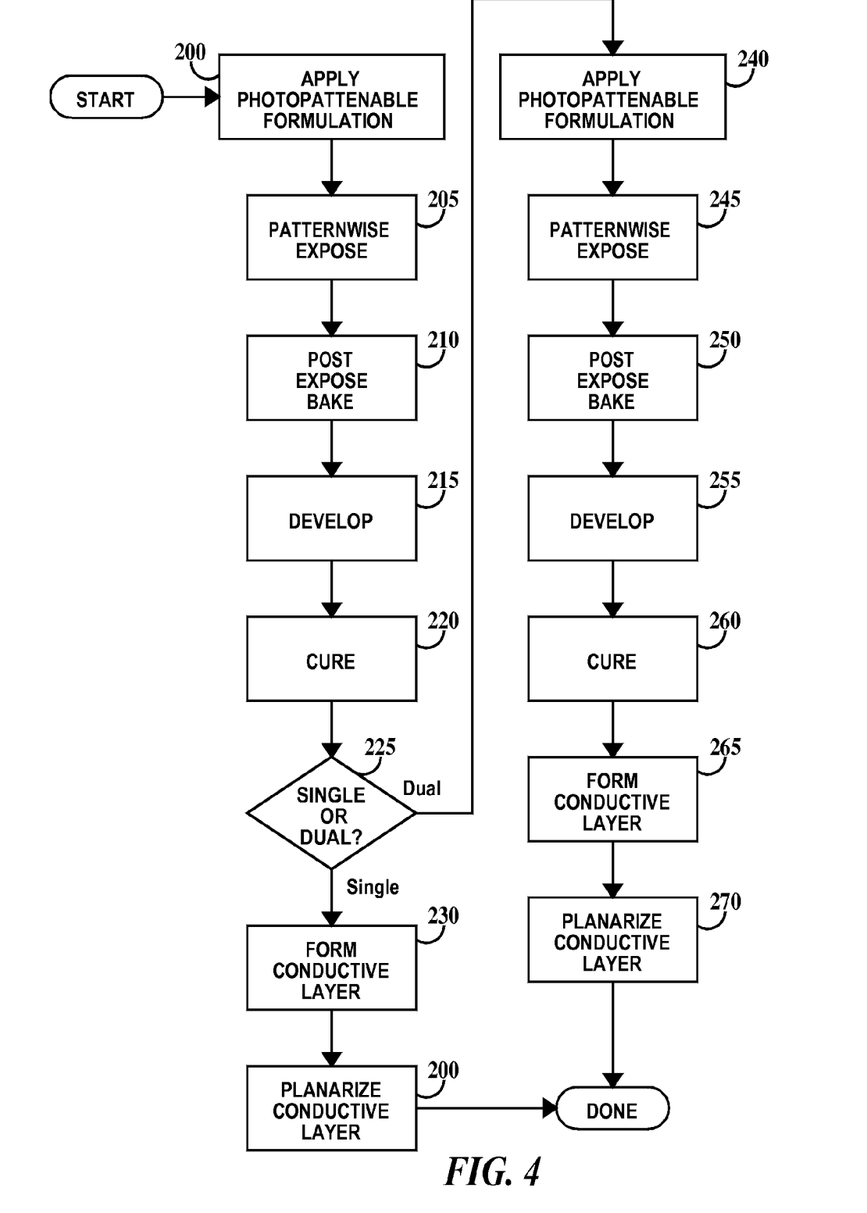
FIG. 4 is a flowchart describing a method of forming single- and dual damascene wires in dielectric material formed using a negative tone photo-patternable dielectric formulation according to embodiments of the present invention.

FIG. 4 is a flowchart describing a method of forming single- and dual damascene wires in dielectric material formed using a negative tone photo-patternable dielectric formulation according to embodiments of the present invention. In step 200, a negative tone photo-patternable dielectric formulation according to embodiments of the present invention is applied to form a photo-patternable dielectric layer on a substrate (e.g., an integrated circuit undergoing fabrication) as illustrated in FIG. 1A and described supra. In step 205, the photo-patternable dielectric layer is patternwise exposed as illustrated in FIG. 1B and described supra. In step 210, a post exposure bake is performed, in step 215 the exposed photo-patternable dielectric layer is developed, and in step 220, the developed photo-patternable dielectric layer is cured to form a patterned dielectric layer as illustrated in FIG. 1C and described supra.

In step 225, it is decided if the wire to be formed is to be a single-damascene wire or a dual-damascene wire. If a single-damascene wire is to be formed the method proceeds to step 230.

In step 230, an electrically conductive layer as illustrated in FIG. 2A and described supra is formed and in step 235 a planarization process as illustrated in FIG. 2B and described supra is performed to complete fabrication of a single-damascene wire.

Returning to step 225, if a dual-damascene wire is to be formed the method proceeds to step 240. In step 240, a negative tone photo-patternable dielectric formulation according to embodiments of the present invention is applied to form a photo-patternable dielectric layer on a substrate (e.g., an integrated circuit undergoing fabrication) as illustrated in FIG. 3A and described supra. In step 245, the photo-patternable dielectric layer is patternwise exposed as illustrated in FIG. 3B and described supra. In step 250, a post exposure bake is performed, in step 255 the exposed photo-patternable dielectric layer is developed, and in step 260, the developed photo-patternable dielectric layer is cured to form a patterned dielectric layer as illustrated in FIG. 3C and described supra. In step 265, an electrically conductive layer as illustrated in FIG. 3D and described supra is formed and in step 270 a planarization process as illustrated in FIG. 3E and described supra is performed to complete fabrication of a dual-damascene wire.

EXAMPLES

The following examples provide further description of the present invention. The invention is not limited to the details of the examples. Where appropriate, the following techniques and equipment were utilized in the Examples: $^1$H and $^{13}$C NMR spectra were obtained at room temperature on an Avance 400 spectrometer. Quantitative $^{13}$C NMR was run at room temperature in acetone-$d_6$ in an inverse-gated $^1$H-decoupled mode using $Cr(acac)_3$ as a relaxation agent on an Avance 400 spectrometer. Thermo-gravimetric analysis (TGA) was performed at a heating rate of 5° C./min in $N_2$ on a TA Instrument Hi-Res TGA 2950 Thermogravimetric Analyzer. Differential scanning calorimetry (DSC) was performed at a heating rate of 10° C./min on a TA Instruments DSC 2920 modulated differential scanning calorimeter. Molecular weights were measured in tetrahydrofuran (THF) on a Waters Model 150 chromatograph relative to polystyrene standards. IR spectra were recorded on a Nicolet 510 FT-IR spectrometer on a film cast on a KBr plate. Film thickness was measured on a Tencor alpha-step 2000. A quartz crystal microbalance (QCM) was used to study the dissolution kinetics of the resist films in an aqueous tetramethylammonium hydroxide (TMAH) solution (CD-26).

When polymers according to embodiments of the present invention are synthesized using triethoxymethylsilane, the monomer of structural formula (1) is generated with $R^1$ being —$CH_3$, the monomer may be called methylsilsesquioxane. When polymers according to embodiments of the present invention are synthesized using acetoxyethyltriethoxylsilane, the monomer of structural formula (2) is generated with $R^2$ being —$CH_3$, the monomer may be called acetoxyethyltriethoxysilsesquioxane. When polymers according to embodiments of the present invention are synthesized using 2-(triethoxysilyl)ethyl pivalate, the monomer of structural formula (2) is generated with $R^2$ being —$C(CH_3)_3$, the monomer may be called pivalatoxyethylsilsesquioxane. When polymers according to embodiments of the present invention are synthesized using 2-(triethoxysilyl)ethyl neodecanote, the monomer of structural formula (2) is generated with $R^2$ being —$C_9H_{19}$, the monomer may be called neodecanotoxyethylsilsesquioxane. When terpolymers and quadpolymers according to embodiments of the present invention are synthesized using bis-(triethoxysilyl)ethane, the monomer of structural formula (3) is generated with $R^3$ being —$CH_2$—$CH_2$— and the monomer may be called bis-(silsequioxyl)ethane. When terpolymers and quadpolymers according to embodiments of the present invention are synthesized using tetraethoxysilane, the monomer of structural formula (4), the monomer may be called tetraethoxysilane.

Example 1

Synthesis of Aetoxyethyltriethoxysilane

A 250 milliliter (ml) two-necked round-bottom flask equipped with a dropping funnel, magnetic stirrer, and condenser with nitrogen inlet was charged with chloroplatinic (IV) acid hexahydrate (0.1 g, $0.193 \times 10^{-3}$ mole) and triethoxysilane (50 g, 0.30 mole). The mixture was heated at 80° C. with stirring under nitrogen until the solution turned black (~15 minutes). At this juncture, the heating to the reaction mixture was discontinued and vinyl acetate (43 g, 0.5 mole) was added dropwise to the reaction mixture. The dropwise addition of vinyl acetate led to a exothermic self-sustaining hydrosilylation reaction. After the addition of vinyl acetate, the solution was stirred at room temperature for 2 hours. The product acetoxyethyltriethoxysilane was fractionally distilled from the solution at reduced pressure. Yield ~95%.

Example 2

Synthesis of Pivalatoxyethyltriethoxysilane

A 250 ml two-necked round-bottom flask equipped with a dropping funnel, magnetic stirrer, and a condenser with nitrogen inlet was charged with chloroplatinic(IV) acid hexahydrate (0.1 g, $0.193 \times 10^{-3}$ mole) and triethoxysilane (50 g, 0.30 mole). The mixture was heated at 80° C. with stirring under nitrogen until the mixture turned black (~15 minutes). At this juncture, the heating to the reaction mixture was discontinued and vinyl pivalate (38.9 g, 0.30 mole) was added dropwise to the reaction mixture. The dropwise addition of vinyl pivalate led to a exothermic self-sustaining hydrosilylation reaction. After the addition of vinyl pivalate, the solution was stirred at room temperature for 2 hours. The product pivalatoxyethyltriethoxysilane was fractionally distilled from the solution at reduced pressure. Yield ~95%.

Example 3

Synthesis of Neodecanotoxyethyltriethoxysilane

A 250 mL two-necked round-bottom flask equipped with a dropping funnel, magnetic stirrer, and condenser with nitrogen inlet was charged with chloroplatinic(IV) acid hexahydrate (0.1 g, $0.193 \times 10^{-3}$ mole) and triethoxysilane (50 g, 0.30 mole). The mixture was heated at 80° C. with stirring under nitrogen until the mixture turned black (~15 minutes). At this juncture, the heating to the reaction mixture was discontinued and vinyl neodecanoate (60 g, 0.30 mole) was added dropwise to the reaction mixture. The dropwise addition of vinyl neodecanoate led to a exothermic self-sustaining hydrosilylation reaction. After the addition of vinyl neodecanoate, the solution was stirred at room temperature for 2 hours. The mixture was then stirred overnight with activated charcoal (0.2 g) and the product neodecanotoxyethyltriethoxysilane was recovered by filtering the solution. Yield ~95%.

Example 4

Synthesis of Poly[methylsilsesquioxane-co-acetoxyethylsilsesquioxane-co-bis-silsesquioxylethane-co-tetraethoxysilane]

A 250 milliliter (ml) three neck round-bottom flask equipped with a thermocouple thermometer, magnetic stirrer, condenser with nitrogen inlet, and a temperature controlled heating mantle was charged with a mixture of triethoxymethylsilane (39.23 grams, 0.22 mole), acetoxyethyltriethoxysilane (10.01 g, 0.04 mole), tetraethoxysilane (8.33 grams, 0.04 mole), bis(triethoxysilyl)ethane (28.36 g, 0.08 moles), and 67.5 grams of methyl isobutyl ketone. The mixture was heated with stirring under nitrogen and 25.2 ml of a 1.75 wt % solution of oxalic acid in water was added to the above mixture at 50° C. The reaction mixture was initially inhomogeneous, but after 15 minutes of stirring became homogeneous. The homogenization of the reaction mixture was accompanied by the exothermic reaction leading to increase in temperature to around 80° C. The temperature was brought down to 50° C. and the mixture was stirred for a total of 5 hours. Thereafter, the mixture was cooled to room temperature and diluted with 150 ml of ethyl acetate. This mixture was extracted with eight 100 ml portions of deionized water (final water extract was almost neutral to pH paper). The organic layer was evaporated to yield 24.0 grams of hard foam after evacuation at high vacuum and room temperature for 24 hours. The molar ratio of monomers (1), (2), (3) and (4) was 11:2:4:2.

Example 5

Synthesis of Poly[methylsilsesquioxane-co-pivalatoxyethylsilsesquioxane-co-bis-(silsesquioxyl) ethane-co-tetraethoxysilane]

A 250 ml three neck round-bottom flask equipped with a thermocouple thermometer, magnetic stirrer, condenser with nitrogen inlet, and a temperature controlled heating mantle was charged with a mixture of triethoxymethylsilane (39.23 grams, 0.22 mole), 2-(triethoxysilyl)ethyl pivalate (11.68 g, 0.04 mole), tetraethoxysilane (8.33 grams, 0.04 mole), bis(triethoxysilyl)ethane (28.36 g, 0.08 mole), and 67.5 grams of methyl isobutyl ketone. The mixture was heated with stirring under nitrogen and 25.2 ml of a 1.75 wt % solution of oxalic acid in water was added to the above mixture at 50° C. The reaction mixture was initially inhomogeneous, but after 15 minutes of stirring became homogeneous. The homogenization of the reaction mixture was accompanied by the exothermic reaction leading to an increase in temperature to around 80° C. The temperature was brought down to 50° C. and the mixture was stirred for a total of 5 hours. Thereafter, the mixture was cooled to room temperature and diluted with 150 ml of ethyl acetate. This mixture was extracted with eight 100 ml portions of deionized water (final water extract was almost neutral to pH paper). The organic layer was evaporated to yield 23.2 grams of hard foam after evacuation at high vacuum and room temperature for 24 hours. The molar ratio of monomers (1), (2), (3) and (4) was 11:2:4:2.

Example 6

Synthesis of Poly[methylsilsesquioxane-co-neodecanotoethylsilsesquioxane-co-bis-(silsesquioxyl) ethane-co-tetraethoxysilane]

A 250 ml three neck round-bottom flask equipped with a thermocouple thermometer, magnetic stirrer, condenser with nitrogen inlet, and a temperature controlled heating mantle was charged with a mixture of triethoxymethylsilane (39.23 grams, 0.22 mole), 2-(triethoxysilyl)ethyl neodecanoate (14.48 g, 0.04 mole), tetraethoxysilane (8.33 grams, 0.04 moles), bis(triethoxysilyl)ethane (28.36 g, 0.08 moles), and 67.5 grams of methyl isobutyl ketone. The mixture was heated with stirring under nitrogen and 25.2 ml of a 1.75 wt % solution of oxalic acid in water was added to the above mixture at 50° C. The reaction mixture was initially inhomogeneous, but after 15 minutes of stirring became homogeneous. The homogenization of the reaction mixture was accompanied by the exothermic reaction leading to increase in temperature to around 80° C. The temperature was brought down to 50° C. and the mixture was stirred for a total of 5 hours. Thereafter, the mixture was cooled to room temperature and diluted with 150 ml of ethyl acetate. This mixture was extracted with eight 100 ml portions of deionized water (final water extract was almost neutral to pH paper). The organic layer was evaporated to yield 21.7 grams of hard foam after evacuation at high vacuum and room temperature for 24 hours. The molar ratio of monomers (1), (2), (3) and (4) was 11:2:4:2.

Example 7

Synthesis of Poly[Methylsilsesquioxane-co-Neodecanotoxyethylsilsesquioxane-co-Tetraethoxysilane-co-Bis-(silsesquioxyl)ethane]9:5:2:5

A 250 ml three neck round-bottom flask equipped with a thermocouple thermometer, magnetic stirrer, condenser with nitrogen inlet, and a temperature controlled heating mantle was charged with a mixture of triethoxymethylsilane (16.05 grams, 0.09 moles), 2-(triethoxysilyl)ethyl neodecanoate (18.1 g, 0.05 mole), tetraethoxysilane (4.16 grams, 0.02 moles), bis(triethoxysilyl)ethane (17.73 g, 0.05 moles), and 50 grams of methyl isobutyl ketone. The mixture was heated with stirring under nitrogen and 12 ml of a 1.75 wt % solution of oxalic acid in water was added to the above mixture at 50° C. The reaction mixture was initially inhomogeneous, but after 15 minutes of stirring became homogeneous. The homogenization of the reaction mixture was accompanied by the exothermic reaction leading to increase in temperature to around 70° C. The temperature was brought down to 50° C. and the mixture was stirred for a total of 5 hours. Thereafter, the mixture was cooled to room temperature and diluted with 100 ml of ethyl acetate. This mixture was extracted with eight 100 ml portions of deionized water (final water extract was almost neutral to pH paper). The organic layer was evaporated to yield 15 grams of hard foam after evacuation at high vacuum and room temperature for 24 hours.

Example 8

Dielectric Constant

Dielectric constants were measured for cured samples of each of the polymers of examples 1, 2 and 3. Films of the polymers were spin applied onto silicon wafers and then post-applied baked at 110° C. for 1 min, exposed to 248 nm light, post-exposure baked at 110° C. for 1 min, and then thermally cured at 400° C. The dielectric constant for the polymers described in examples 4, 6 and 7 was 2.88, 2.86, and 2.80 respectively.

Example 9

Photo-Patternable Composition

A patternable low-k composition was formulated with 16.5 wt % solution of Poly[methylsilsesquioxane-co-acetoxyethylsilsesquioxane-co-bis-(silsesquioxyl)ethane-co-tetraethoxysilane] and 2 wt % of triphenylsulfonium nonaflate in PGMEA, and 0.6 parts of an organic base. The resulting low-k formulation was filtered through a 0.2 µm filter. The low-k composition was spin coated onto an 8 inch silicon wafer and pre-exposure baked at 110° C. for 60 s, patternwise exposed to 248 nm UV light on an ASML (0.63 NA, 5/8 annular) DUV stepper, and post exposure baked at 110° C. for 60 s. This was followed by a 30 second puddle development step with 0.26 N TMAH developer to resolve 0.190 µm line and space features.

Example 10

Elastic Modulus

Elastic modulus was measured for cured samples of each of the polymers of examples 4, 5, 6 and 7 using surface acoustics wave spectroscopy (SAWS). Films of the polymers were spin applied onto silicon wafers and then post-applied baked at 110° C. for 1 min, exposed to 248 nm light, post-exposure baked at 110° C. for 1 min, and then thermally cured at 400° C. The elastic modulus for the corresponding polymer films described in examples 4, 5, 6 and 7 was 8.97, 8.8, 8.67, and 6.32 GPa respectively.

Thus the embodiments of the present invention provide patternable dielectric materials, photo-sensitive formulations containing patternable dielectric materials, methods of using photo-sensitive formulations containing patternable dielectric materials in the fabrication of integrated circuits, and integrated circuit structures comprising patternable dielectric materials. The methods according to embodiments of the present invention use less materials and require less steps than conventional methods.

The description of the embodiments of the present invention is given above for the understanding of the present invention. It will be understood that the invention is not limited to the particular embodiments described herein, but is capable of various modifications, rearrangements and substitutions as will now become apparent to those skilled in the art without departing from the scope of the invention. Therefore, it is intended that the following claims cover all such modifications and changes as fall within the true spirit and scope of the invention.

What is claimed is:

1. A method of preparing an organo-silicon compound, wherein said compound comprises:

wherein $R^5$ is an alkyl moiety containing 4 to 20 carbon atoms and $R^6$ is selected from the group consisting of halogens, alkanoates, amines, and alkoxides; and the method comprising:

adding a compound of the structure:

to a compound of the structure:

in the presence of a chloroplatinic acid.

2. The method of claim 1, wherein $R^5$ is tert-butyl or neodecanyl and $R^6$ is —O—$C_2H_5$.

3. The method of claim 1, wherein $R^5$ is tert-butyl.

4. The method of claim 1, wherein $R^5$ is neodecanyl.

5. The method of claim 1, wherein $R^6$ is —O—$C_2H_5$.

6. The method of claim 1, wherein $R^5$ is methyl and $R^6$ is —O—$C_2H_5$.

7. The method of claim 1, wherein $R^5$ is neodecanyl and $R^6$ is —O—$C_2H_5$.

8. The method of claim 1, wherein said is added to a heated mixture said chloroplatinic acid and said 9. The method of claim 8, including performing the preparation under nitrogen.

10. A method of preparing an organo-silicon compound, wherein said compound comprises:

wherein $R^5$ is neodecanyl and $R^6$ is selected from the group consisting of halogens, alkanoates, amines, and alkoxides; and the method comprising:

adding a compound of the structure:

to a compound of the structure:

in the presence of a chloroplatinic acid.

11. The method of claim 10, wherein $R^6$ is —$OC_2$—$H_5$.

12. The method of claim 10, wherein said is added to a heated mixture said chloroplatinic acid and said 13. The method of claim 12, including performing the preparation under nitrogen.

* * * * *